US00PP37555P2

(12) United States Plant Patent
van Noort

(10) Patent No.: US PP37,555 P2
(45) Date of Patent: Aug. 4, 2026

(54) ***GERANIUM* PLANT NAMED 'MVNG202130'**

(50) Latin Name: *Geranium macrorrhizum*
Varietal Denomination: MVNG202130

(71) Applicant: Marco van Noort, Warmond (NL)

(72) Inventor: Marco van Noort, Warmond (NL)

(73) Assignee: MARCO VAN NOORT BREEDING B.V., Warmond (NL)

( * ) Notice: Subject to any disclaimer, the term of this patent is extended or adjusted under 35 U.S.C. 154(b) by 0 days.

(21) Appl. No.: 19/417,499

(22) Filed: Dec. 12, 2025

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./324
CPC ..... A01H 5/02; A01H 5/00; A01H 6/42
See application file for complete search history.

*Primary Examiner* — June Hwu
(74) *Attorney, Agent, or Firm* — Penny J. Aguirre

(57) ABSTRACT

A new cultivar of *Geranium macrorrhizum* plant named 'MVNG202130' that is characterized by its strong and healthy plant habit with disease resistance to *Fusarium* sp., its flowers that are large in size and with petals that are light purple-white in color and sepals and stamens that are purple-red in color, and its floriferous blooming habit.

3 Drawing Sheets

Botanical classification: *Geranium macrorrhizum.*
Cultivar designation: 'MVNG202130'.

CROSS REFERENCE TO A RELATED APPLICATION

This application is related to a European plant breeders' rights application filed on Mar. 13, 2024, application No. 2024/0646. The Applicant received the information for the plant breeders' rights application directly from the Inventor.

BACKGROUND OF THE INVENTION

The present invention relates to a new and distinct cultivar of *Geranium* plant, botanically known as *Geranium macrorrhizum* 'MVNG202130' and will be referred to hereafter by its cultivar name, 'MVNG202130'. 'MVNG202130' is a new cultivar of herbaceous perennial grown for use as a garden plant.

'MVNG202130' arose from an on going breeding program conducted by the Inventor in Warmond, The Netherlands. The goal of the breeding program is to develop new cultivars of *Geranium* that have healthy growth habits, resistance to disease, and a long lifespan.

The new cultivar arose from a cross made by the Inventor in Warmond, The Netherlands in May of 2018 between an unnamed and unpatented proprietary selection of *Geranium macrorrhizum* as the female parent and *Geranium macrorrhizum* 'White Ness' (not patented) as the male parent. The Inventor selected 'MVNG202130' as a single unique plant amongst the seedlings that resulted from the above cross in June of 2019.

Asexual propagation of the new cultivar was first accomplished by tissue culture using meristematic tissue under the direction of the Inventor in Warmond, The Netherlands in August of 2023. Asexual propagation by tissue culture tissue and stem cuttings has determined that the characteristics of the new cultivar are stable and are reproduced true to type in successive generations.

SUMMARY OF THE INVENTION

The following traits have been repeatedly observed and represent the characteristics of 'MVNG202130'. These attributes in combination distinguish 'MVNG202130' as a new and distinct cultivar of *Geranium.*

1. 'MVNG202130' exhibits a strong and healthy plant habit with disease resistance to Fusarium sp.
2. 'MVNG202130' exhibits flowers that are large in size and with petals that are light purple-white in color and sepals and stamens that are purple-red in color.
3. 'MVNG202130' exhibits a floriferous blooming habit.

The female parent of 'MVNG202130' differs from 'MVNG202130' in having a less floriferous blooming habit, smaller plant size, and a higher disease susceptibility. The male parent of 'MVNG202130' differs from 'MVNG202130' in having lighter green foliage, a less robust plant habit, smaller flowers, and a less floriferous blooming habit. 'MVNG202130' can be most closely compared to the *Geranium macrorrhizum* 'Spessart' (not patented) and *Geranium cantabrigiense* 'Biokovo' (not patented). 'Spessart' is similar to 'MVNG202130' in being suitable for use as a ground cover. 'Spessart' differs from 'MVNG202130' in having lighter green foliage, a weaker growth habit, a higher susceptibility to *Fusarium*, and flowers that are slightly whiter in color. 'Biokovo' is similar to 'MVNG202130' in having white flowers and in being suitable for use as a ground cover. 'Biokovo' differs from 'MVNG202130' in having a shorter plant height, a less robust growth habit, a higher susceptibility to Fusarium, leaves that are smaller in size, and shorter pedicels.

BRIEF DESCRIPTION OF THE DRAWINGS

The accompanying color photographs illustrate the overall appearance and distinct characteristics of the new *Gera-*

*nium*. The photographs were taken of one year-old plants of 'MVNG202130' as grown in a 27-cm container outdoors in Warmond, The Netherlands.

Figure 1:
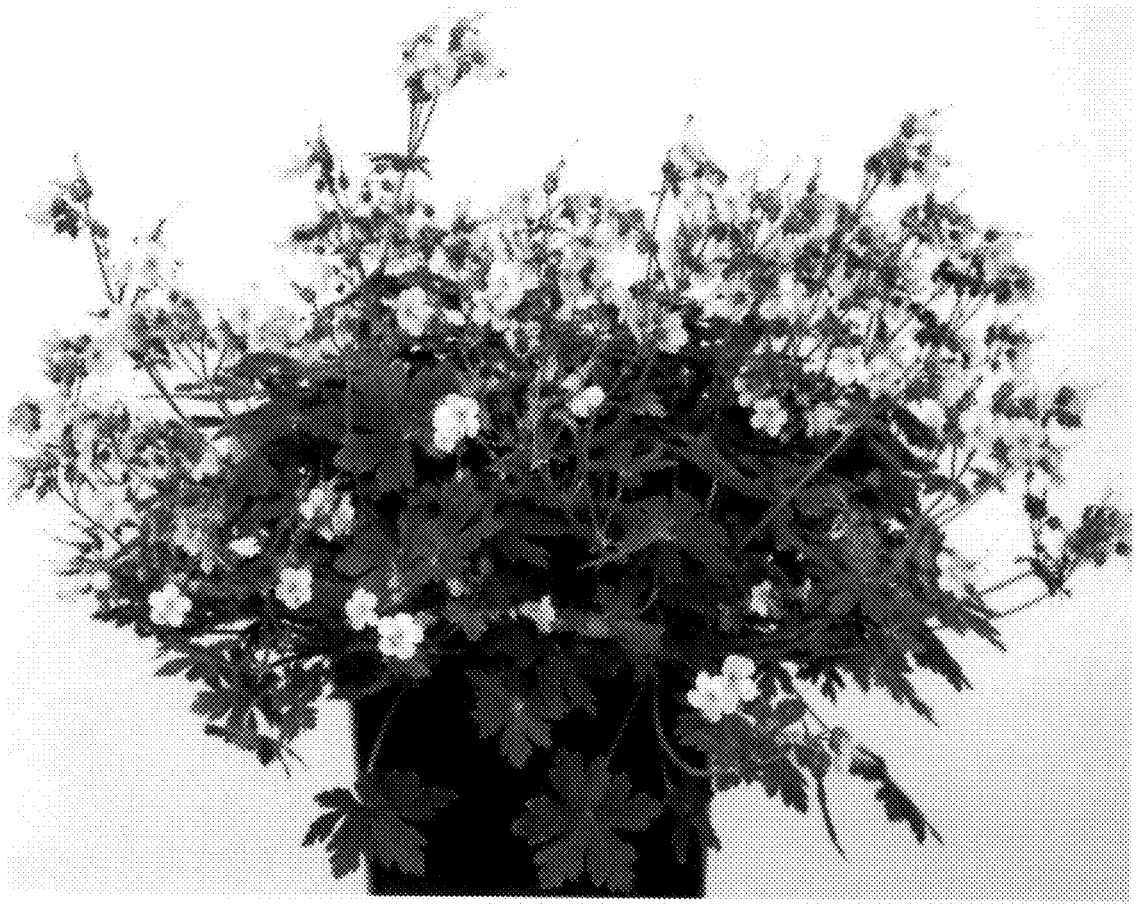

The photograph in FIG. 1 provides a view of 'MVNG202130' in bloom.

Figure 2:
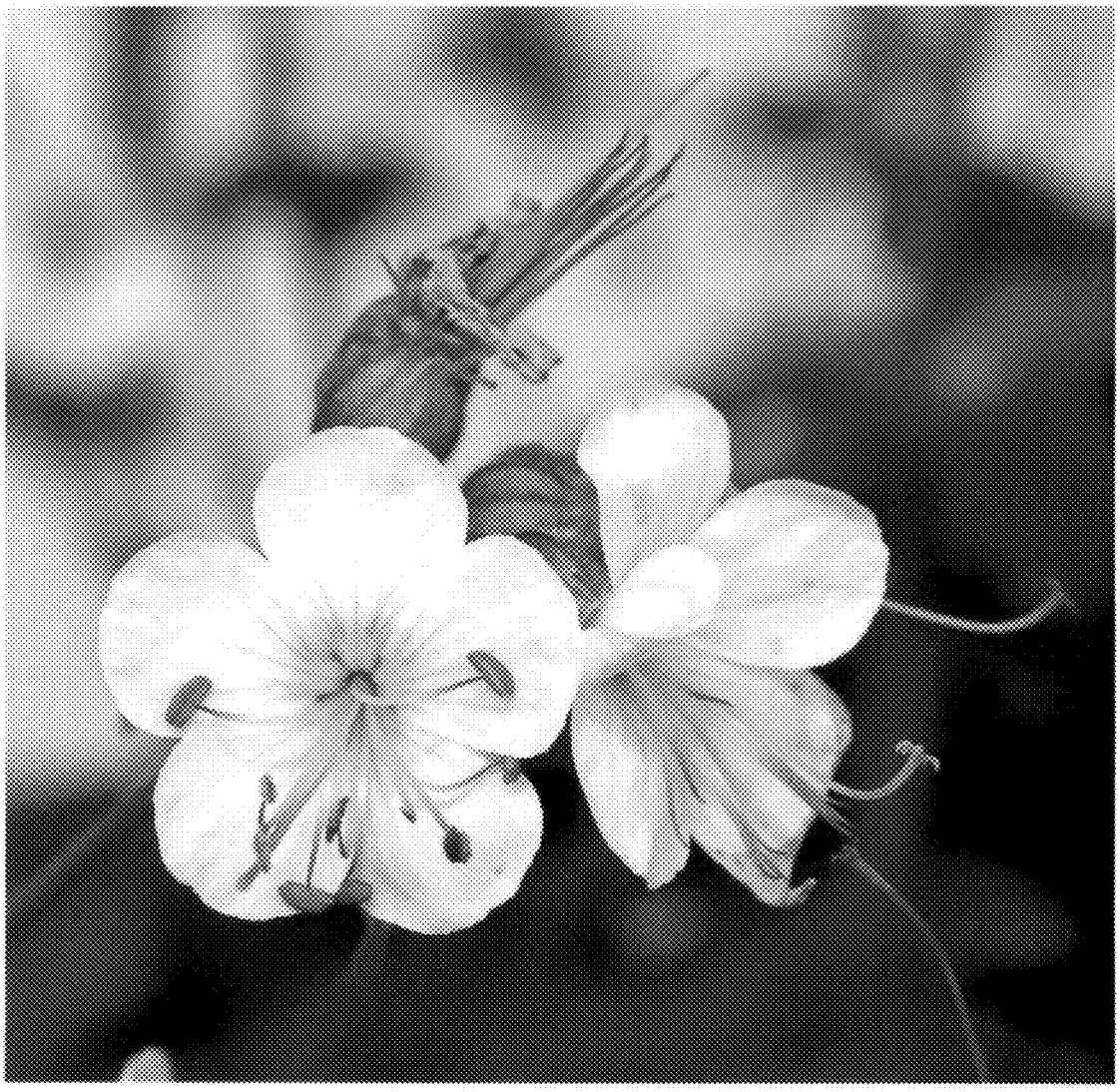

The photograph in FIG. 2 provides a close-up view of the flowers of 'MVNG202130'.

Figure 3:
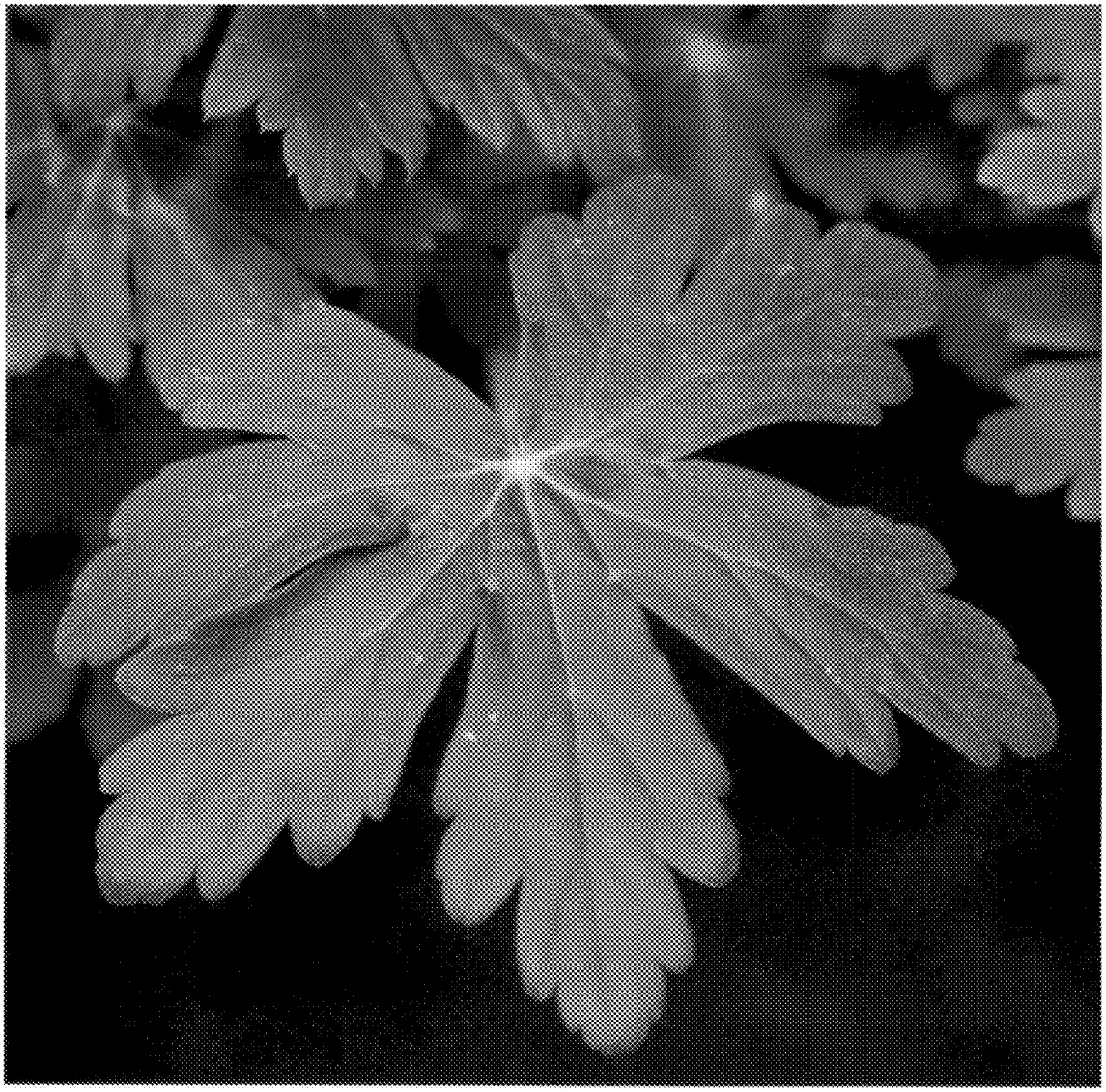

The photograph in FIG. 3 provides a close-up view of the foliage of 'MVNG202130'.

The colors in the photographs are as close as possible with the digital photography and printing techniques utilized and the color codes in the detailed botanical description accurately describe the colors of the new *Geranium*.

DETAILED BOTANICAL DESCRIPTION OF THE PLANT

The following is a detailed description of one year-old plants of the new cultivar as grown outdoors in 27-cm containers in Warmond, The Netherlands. The phenotype of the new cultivar may vary with variations in environmental, climatic, and cultural conditions, as it has not been tested under all possible environmental conditions. The color determination is in accordance with the 2015 $6^{th}$ edition (2019 reprint) Colour Charts of The Royal Horticultural Society, London, England, except where general color terms of ordinary dictionary significance are used.

General characteristics:

*Blooming period*.—April to June in The Netherlands.

*Plant type*.—Herbaceous perennial.

*Plant habit*.—Flattened globular, broadly spreading, upright, suitable as a ground cover.

*Height and spread*.—Average of 40 cm in height and 80 cm in spread as grown in the landscape.

*Hardiness*.—At least in U.S.D.A. Zones 4 to 9.

*Diseases and pests*.—Has shown high resistance to *Fusarium* sp., no resistance or susceptibility has been observed to pests.

*Root description*.—Slightly fleshy, overall average diameter of the root system is 2 mm, both shallow and moderately deep distribution into the soil, moderate density, moderately branched, smooth and glabrous surfaces, 164C in color.

*Root development*.—Average of 2 weeks for root initiation, 12 weeks to produce a fully rooted cutting.

*Propagation*.—Stem cuttings and tissue culture.

Branch description:

*Branch size*.—Average of 7.6 cm in length and 9 mm in width.

*Branch shape*.—Round.

*Branch strength*.—Moderately strong.

*Branch aspect*.—Average of 50° (varying between 80° and 20°).

*Branch color*.—Young; 145B, mature; 166B, internodes; 166A.

*Branch surface*.—Very slightly glossy, glabrous.

*Internode length*.—Average of 4 mm.

*Branching habit*.—Average of 26 branches, basal rosette, forming short herbaceous stems, no lateral branching.

Foliage description:

*Leaf shape*.—Reniform (overall shape), palmately cleft with an average of 7 lobes.

*Leaf division*.—Simple.

*Leaf base*.—Hastate, lobes free.

*Leaf apex*.—Flat to very slightly concave.

*Leaf fragrance*.—Typical *Geranium* scent when crushed.

*Leaf venation*.—Palmate, upper surface 145A, lower surface 146C.

*Leaf margins*.—Lanciniate.

*Leaf lobes*.—Sinuses are deep, sinus orientation is divergent.

*Leaf attachment*.—Petiolate.

*Leaf arrangement*.—Alternate.

*Leaf surface*.—Both surfaces non-rugose, matte, moderately to densely covered with tomentose short hairs; 0.5 mm in length, N155A in color.

*Leaf color*.—Young upper surface; 143A, lobe axils dotted 144B, young lower surface; 138B, lobe axils dotted 144B, mature upper surface; 137B, lobe axils dotted 145A, mature lower surface; 138B, lobe axils dotted 146C.

*Leaf size*.—Average of 8.5 cm in length and 9.7 cm in width.

*Leaf quantity*.—Average of 20 per basal branch.

*Petioles*.—Average of 14.6 cm in length and 2.5 mm in width, color; upper surface a blend of 144A and 146B, lower surface 144A, both surfaces are slightly glossy, densely covered with short tomentose hairs an average of 1 mm in length and a blend of N155A and 156D in color.

*Stipules*.—2 leafy stipules, present at the base of the leaves, narrow deltoid in shape, acute apex, broadly cuneate base, an average of 8 mm in length and 4 mm in width, color on both surfaces; transparent; 157B with main vein 143B.

Flower description:

*Inflorescence type*.—Compound cyme.

*Inflorescence size*.—Average of 28.9 cm in height, 13.2 cm in diameter.

*Lastingness of flowers*.—Average of 7 days, self cleaning.

*Flowers*.—An average of 20 per inflorescence, 300 per plant, 2,000 flowers and buds per plant.axillary arrangement, rotate, single, average of 2.6 cm in height, 2.6 cm in diameter, 2.5 cm in depth, outward facing.

*Flower fragrance*.—None.

*Flower buds*.—An average of 1.1 cm in length, 7 mm in width, color; 185B, axially ribbed 147A, broadly elliptic to near spherical in shape, mucronate sepal tips on top, surface is very slightly glossy, densely covered with short glandular hairs an average of 0.5 mm in length and 156D in color.

*Petals*.—5, rotate in arrangement, 1 whorl, spathulate in shape, narrow acuminate base, rounded apex, entire margins, surfaces are glabrous, smooth, slightly velvety, and matte, average of 1.7 cm in length, 1.1 cm in width, color; when opening upper and lower surface 76D and 155A, veined 76C to 76D, veins 76C to 76D, when opening and fully open lower surface 76D and N155A, veins 76C to 76D, dropped at maturity.

*Calyx*.—Rotate, average of 8 mm in length and 1 cm in width.

*Sepals*.—Average of 5, 1 whorl, broadly ovate in shape, entire margins, mucronate apex, cuneate base, average of 1.2 cm length, 7 mm in width, color; when opening upper and lower surface 185B, apex and axially veined 147B, when fully open upper surface 187D, apex 147B, veins 147B, when fully open lower surface 187D, apex 183A, veins 183A upper surface glabrous, smooth, slightly glossy, lower surface glabrous, smooth, matte and densely covered with short tomentose hairs; 0.5 mm in length, a blend of N155A and 156D in color.

*Peduncles*.—Average angle of both primary and secondary 40° to stem, primary; 19.8 cm in length and 3 mm in diameter, color 144A with upper surface moderately to strongly tinged 177A, secondary; 4.4 cm in length and 1.5 mm in width, color 148A with upper surface moderately to strongly tinged 177A, surfaces are slightly glossy and densely covered with short soft tomentose hairs; 0.1 mm in length, color a blend of N155A and 156D.

*Pedicels*.—Average angle of 45°, 178A in color, 1 cm in length, 1 mm in diameter, surfaces are slightly glossy and densely covered with short soft tomentose hairs; 0.5 mm in length, N155A in color.

*Floral bracts*.—4 bracts are placed at the base of each secondary peduncle, lanceolate in shape, acuminate apex, clasping at base, average of 3 mm in length and 1.5 mm in width, both surfaces glabrous and 145B in color.

Reproductive organs:

*Gynoecium*.—Pistil; 1, average of 2.4 cm in length, stigmas; 5, star-shaped, 1 mm in length, 0.75 mm in diameter, 163D in color, style; average of 2.3 mm in length, color; 158D, ovary; 144C in color.

*Androecium*.—Stamens; 10, anthers; narrow oblong in shape, 2.5 mm in length, 1 mm in width, 179A and 179B in color, filaments; 1.6 cm in length, N155D in color and fading to 186B at distal end, pollen is moderate in quantity and 12A in color.

*Fruit/seeds*.—None observed to date.

It is claimed:

1. A new and distinct cultivar of *Geranium* plant named 'MVNG202130' as herein illustrated and described.

* * * * *